Jan. 26, 1937. A. L. MILLER Plant Pat. 227
GLADIOLUS
Filed April 3, 1936
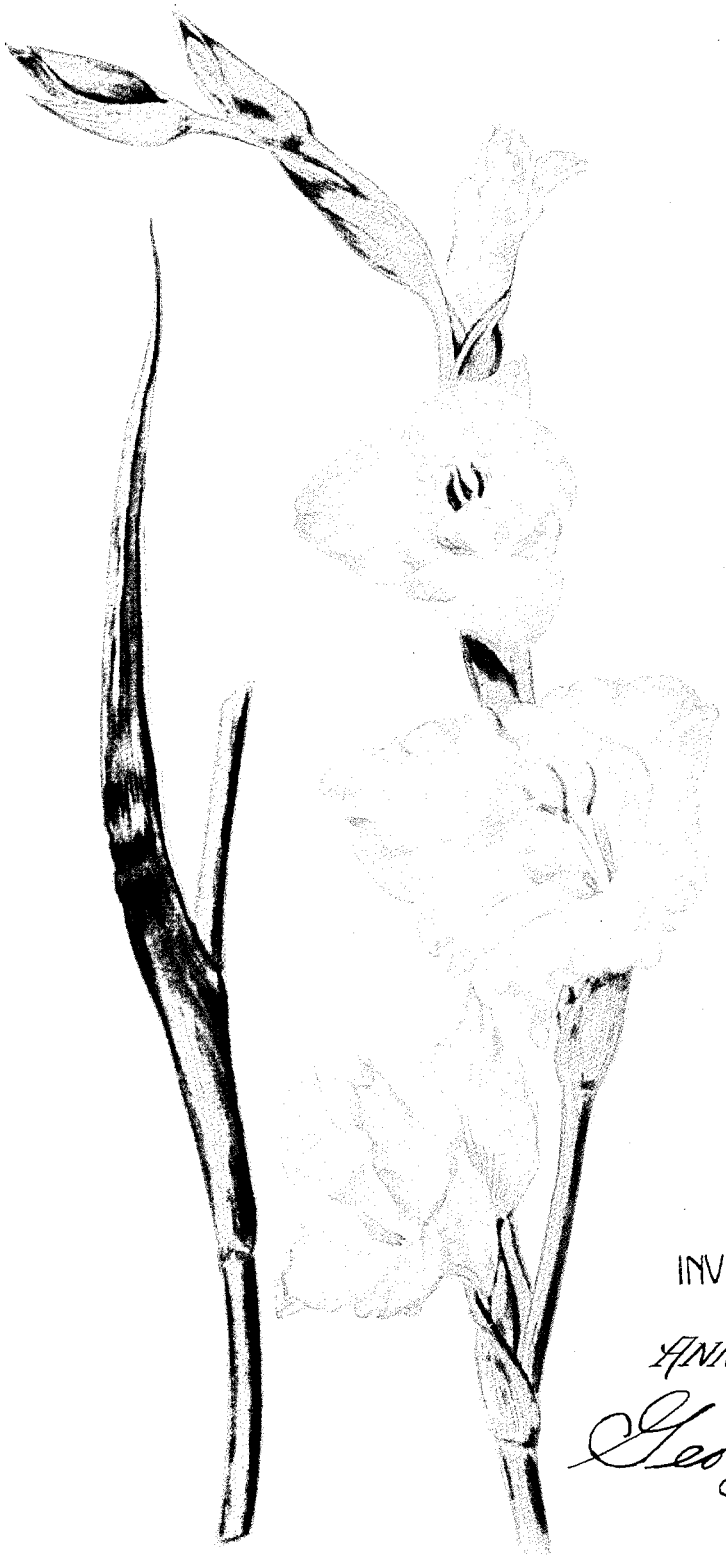
INVENTOR
ANNA L. MILLER.
George E. Cook.
ATTORNEY.

Patented Jan. 26, 1937

Plant Pat. 227

UNITED STATES PATENT OFFICE

227

GLADIOLUS

Anna L. Miller, Nashport, Ohio

Application April 3, 1936, Serial No. 72,647

1 Claim. (Cl. 47—60)

My invention relates to improvements in the usual type of flowering gladiolus grown in gardens and for cut flower purposes. In addition to other desirable qualities hereinafter set forth my new gladiolus has a fragrant odor, a quality very rare in gladioli.

This new variety is the result of long and complicated cross breeding carried on by myself, using unnamed primulinus hybrids, destroying the unpromising seedlings and gradually developing desirable features. The original of this new variety first bloomed in 1927. Its fragrance attracted attention but it was not until 1929 that the bulb matured and produced a beautiful spike of flowers. Trials in widely separated localities have since proved that this variety reproduces properly and retains its ability to produce a fragrant odor.

The accompanying illustration shows part of a spike of this new variety of gladiolus with the lower floret past its prime and withering, the second fully opened and in its prime, the third partly opened, and above this a floret just beginning to unroll, and others barely showing color. The illustration also shows a section of stem and the first leaf below the flower spike.

*The plant*

The plant is a vigorous grower, flower spikes reaching an average height of four to five feet with stalks from large bulbs, amply watered, growing to a height of six feet.

It is of primulinus type, that is, producing a wiry growth with slender leaves. Foliage is rather sparse since the leaves on the flower stems are slender and rather short. The topmost leaf on a flower stem seldom rises nearer than 5 to 6 inches below the bottom floret on the spike. The color of the leaf is "Light Elm Green" (Plate XVII Ridgway's Color Standards and Nomenclature).

The stems are strong and sturdy, entirely capable of holding the flower spike upright. The color of the lower part of the stem is approximately the same as that of the foliage, but the upper half of the stem on the side which is exposed to the sun has a brownish appearance and the sheaths that spring from the stem and encase the bases of the florets have streaks and splotches approaching pink in color.

Each stem ordinarily has 8 to 10 buds or florets. Normally at a given time one floret is fully opened, the one above half opened and the one below half closed. Ordinarily two additional buds will show considerable color at this same time.

The florets are regularly spaced on the stem in pleasing form, not too close together to cause crowding and malformation. While the tight buds lie flat to the stem, as each opens it turns at right angles to the stem and the open flower presents a full front view.

*The flower*

The bud when beginning to push out of its sheath shows first a dark red, approaching "Nopal Red" (Plate I, Ridgway's Color Standards and Nomenclature) and as it protrudes farther the "Yellow-green" (Plate VI) portions of the petals appear.

The fully opened flower (floret) measures 3 to 3¼ inches across and consists of six petals regularly arranged in two rows in typical, slightly hooded gladiolus form with the two larger petals above in the outer row and one large petal above in the inner row. The petals are somewhat curled and considerably folded.

Three heavy white stamens rise from the base of the carolla, curving so as to lie along the upper inner surface and each terminates in large "Lavender-violet" (Plate XXV) anthers well covered with pollen. These lavender-violet anthers constitute a prominent and pleasing feature of the flower. The single white style, which is slightly longer than the combined stamens and anthers, terminates in three short curling branches.

*Color.*—The predominant colors are red, ranging from "Begonia Rose" to "Nopal Red" (Plate I, Ridgway's Color Standards and Nomenclature) and yellow, ranging from "Lemon Chrome" to "Apricot Yellow" (Plate IV). The yellow is found on the basal portions of the petals, on both the inside and outside surfaces, and covers approximately one-half the surface of the three lower petals in each floret but only a quarter to an eighth of the upper three petals. All the petals have a yellowish midvein.

The red color is found on the outer portions of the petals, the brightest and darkest shades being found at the tips of the outer petals and the color fading rapidly as the mid-areas of the petals are approached, and merging with the yellow farther on toward the base of the petal. Each petal also has an intense Rose Red streak at the point where its edges meet and join with its neighbors to form the basal tube. This bright color is visible on the outside of the flower as a short, narrow streak and in the throat of the flower as a broader, less regular streak or patch.

The *odor* is not strong but increases as the flower ages. The odor has been described by gladiolus experts as similar to that of the species *g. recurvis,* a native of Africa and too tender to be grown in the United States except under glass and in California and Florida. It is believed that this odor can be extracted and used for perfume purposes.

The florets continue to open daily for several days after cutting, thereby giving good lasting qualities.

Having thus disclosed my invention, I claim:

The variety of gladiolus herein described and illustrated, characterized particularly by its long flower stems, its sparse leaf growth, its flowers having distinctive coloring as described and lavender-violet stamens, also by its odor.

ANNA L. MILLER.